United States Patent
Becker et al.

(10) Patent No.: US 6,560,309 B1
(45) Date of Patent: May 6, 2003

(54) METHOD FOR EXAMINING A BODY REGION EXECUTING A PERIODIC MOTION

(75) Inventors: Christoph Becker, Starnberg (DE); Thomas Flohr, Uehlfeld (DE); Bernd Ohnesorge, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/724,055

(22) Filed: Nov. 28, 2000

(30) Foreign Application Priority Data

Nov. 28, 1999 (DE) .......................... 199 57 083

(51) Int. Cl.⁷ .............................................. G01N 23/00
(52) U.S. Cl. .............................................. 378/8; 378/95
(58) Field of Search ........................... 378/95, 8, 4, 16, 378/19, 21, 108, 165

(56) References Cited

U.S. PATENT DOCUMENTS

| 4,868,747 | A | | 9/1989 | Mori et al. | |
|---|---|---|---|---|---|
| 5,379,333 | A | | 1/1995 | Toth | |
| 5,400,378 | A | * | 3/1995 | Toth | 378/16 |
| 5,822,393 | A | | 10/1998 | Popescu | |
| 6,275,560 | B1 | * | 8/2001 | Blake et al. | 378/8 |
| 6,295,331 | B1 | * | 9/2001 | Hsieh | 378/19 |
| 6,320,930 | B1 | * | 11/2001 | Arakawa | 378/8 |
| 6,324,254 | B1 | * | 11/2001 | Pflaum | 378/95 |
| 6,327,326 | B1 | * | 12/2001 | Flohr et al. | 378/8 |

* cited by examiner

*Primary Examiner*—Drew A. Dunn
*Assistant Examiner*—Irakli Kiknadze
(74) *Attorney, Agent, or Firm*—Schiff Hardin & Waite

(57) ABSTRACT

In a method for examining a body region executing a periodic motion in an examination subject with a diagnostic apparatus having a radiation source for generating radiation penetrating the examination subject and a detector system for the radiation emanating from the radiation source, the intensity of the radiation emanating from the radiation source is modulated between a reference value and a reduced value compared to the reference value, substantially synchronously with the movement, so that the reference value is present during a phase of the periodic motion to be imaged with the diagnostic apparatus, and substantially only the data that were output by the detector system during the presence of the reference value of the radiation are utilized for the determination of the image.

15 Claims, 3 Drawing Sheets

METHOD FOR EXAMINING A BODY REGION EXECUTING A PERIODIC MOTION

BACKGROUND OF THE INVENTION

1. Field of the Invention

The present invention is directed to a method for examining a body region in an examination subject, the body region executing a periodic motion within the examination subject, wherein data are acquired from the examination subject while irradiating the examination subject with penetrating radiation.

2. Description of the Prior Art

Examination of the beating heart with a CT apparatus such as, for example, for determining the degree of calcification ("calcium scoring") or for searching for stenosis in the coronary vessels, requires special measures for acquiring images that are low in motion artifacts. The ECG-triggered, sequential exposure technique is currently employed in various models of CT systems such as CT apparatuses of the $3^{rd}$ generation (x-ray source and detector system rotate in common around a system axis) or electron beam CT apparatus as well (EBT=electron beam tomography). The R-wave of the ECG signal of the patient is used to implement a scan at a specific z-position, i.e. at a specific position in the direction of the system axis, in a defined phase of the cardiac cycle. The scan is thereby triggered with a selectable delay after a registered R-wave. The delay, and thus the starting time of the scan following the R-wave are usually to be determined from the current R-R interval duration $T_{RR}$ (for example, as a percentage). Since this must be prospectively estimated from the duration of the preceding cardiac cycles, the method is susceptible to arrhythmia of the heartbeat.

ECG-gated spiral technique is becoming popular for examinations of the heart, particularly with the introduction of multi-slice CT apparatuses, i.e. CT apparatuses having a radiation detector composed of a number of detector lines of individual detectors. With the assistance of the ECG signal, data intervals are retrospectively selected in order to be able to continuously image the heart volume in a defined phase, the selection being made from a scan registered given continuous rotation of x-ray source and detector system around the system axis with simultaneous, continuous displacement of patient and x-ray source relative to one another in the direction of the system axis. This is known as the multi-slice spiral technique and has important advantages over the ECG-triggered sequential exposure technique. The continuous data acquisition allows the reconstruction of overlapping tomograms, and thus a considerable improvement in the 3D image quality. The noticeable increase of the scan speed enables examinations with thinner slice thicknesses during a breath-holding phase, and thus a further improvement of the longitudinal resolution, i.e. the resolution in the direction of the system axis. The position of the data intervals in the cardiac cycle, i.e. of those time intervals during which data that can be interpreted for the reconstruction of tomograms are acquired, is not based on a prospective estimate but on the correctly measured R-R interval lengths $T_{RR}$, so that an enhanced stability of the method given heart rate arrhythmia is achieved. Moreover, the heart volume in an arbitrary phase of the cardiac cycle can be calculated from the same dataset, as basis for functional examinations.

For most applications of retrospectively ECG-gated multi-layer spiral technique, the heart volume is to be reconstructed only in one heart phase, optimally free of motion artifacts. To this end, the gating parameters (delay of the R-wave) are selected such that all images are calculated in the low-motion diastole. This, however, means that the x-ray dose applied outside the correspondingly selected data intervals is not employed for the image reconstruction. Standard methods use, for example, data from a time interval of 350 msec in a cardiac cycle. For a heart cycle duration of 1 sec (pulse 60), this means 65% unused x-ray dose.

SUMMARY OF THE INVENTION

An object of the present invention is to provide a method of the type initially described wherein a body region of an examination subject executing a periodic motion can be registered with reduced dose.

The above object is achieved in accordance with the principles of the present invention in a method for examining a body region which executes a periodic motion in an examination subject, including the steps of irradiating the body region with penetrating radiation and detecting radiation exiting from the examination subject with a detector system which produces output data dependent on the radiation incident thereon, modulating the intensity of the radiation from the x-ray source between a reference and a value that is reduced compared to the reference value, substantially synchronously with the periodic motion, so that the reference value is present during a phase of the periodic motion, and calculating an image of the body region executing the periodic motion using output data from the detector system which were obtained only while radiation having an intensity at the reference value was emitted from the radiation source.

In the inventive method, thus, an ECG-controlled modulation of the x-ray dose is undertaken, for example by controlling the x-ray current, and desired rated dose value thus is reached only in the phase of interest in the cardiac cycle. The inventive method can be technically realized in a simple way and is distinguished by high flexibility and stability given patients with arrhythmia. The modulation of the x-ray dose by an adaptation of the tube current is preferred because of its simplicity. Nonetheless, other procedures such as, forexample, mechanical beam pre-filtering, are conceivable.

A location-dependent modulation of the x-ray dose is currently employed for examinations of, for example, the shoulder and the pelvis but is also employed at the thorax. Here, the x-ray dose is regulated dependent on the anticipated attenuation in the subject for the tube position under consideration in order to obtain a uniform image impression with a reduced overall dose (see U.S. Pat. No. 5,822,393). The inventive ECG-controlled modulation of the x-ray dose can be coupled with this established method, and thus a simultaneously location-dependent and time-dependent modulation of the x-ray dose can be undertaken.

Retrospectively ECG-gated multi-slice spiral technique allows the continuous imaging of the heart volume with thin, overlapping slices in arbitrary phase. A gap-free volume coverage in z-direction within a region dependent on the feed rate, and thus on the pitch can be achieved with suitable reconstruction and weighting methods (for example, projection-dependent weighting among the data of the individual detector lines). The feed rate is selected dependent on the period duration of the heart cycles, i.e. on the cardiac frequency, and taking the detector width into consideration, such that a sub-revolution or full-revolution dataset can be registered in every cardiac cycle and such that the regions covered by successive datasets overlap in z-direction or—in the limit case—abut gap-free. The entire heart volume in the z-direction can then be covered gap-free with tomograms or be displayed in a 3D image. For reconstruction of a 3D image in a specific phase (for example, the diastole) of the cardiac cycle, only data acquired during this phase are utilized for the reconstruction. The selection of the data ensues with a specific time spacing from the most recent R-wave that can, for example retrospectively, be determined as a fixed fraction of the known R-R interval length $T_{RR}$. The x-ray dose by means of the tube current is regulated with the ECG signal such that a specific reference value of the x-ray dose exists during the data registration for this phase, but is otherwise regulated down to a considerably lower value (for example, ⅕ of the reference value).

DESCRIPTION OF THE PREFERRED EMBODIMENTS

Figure 1:
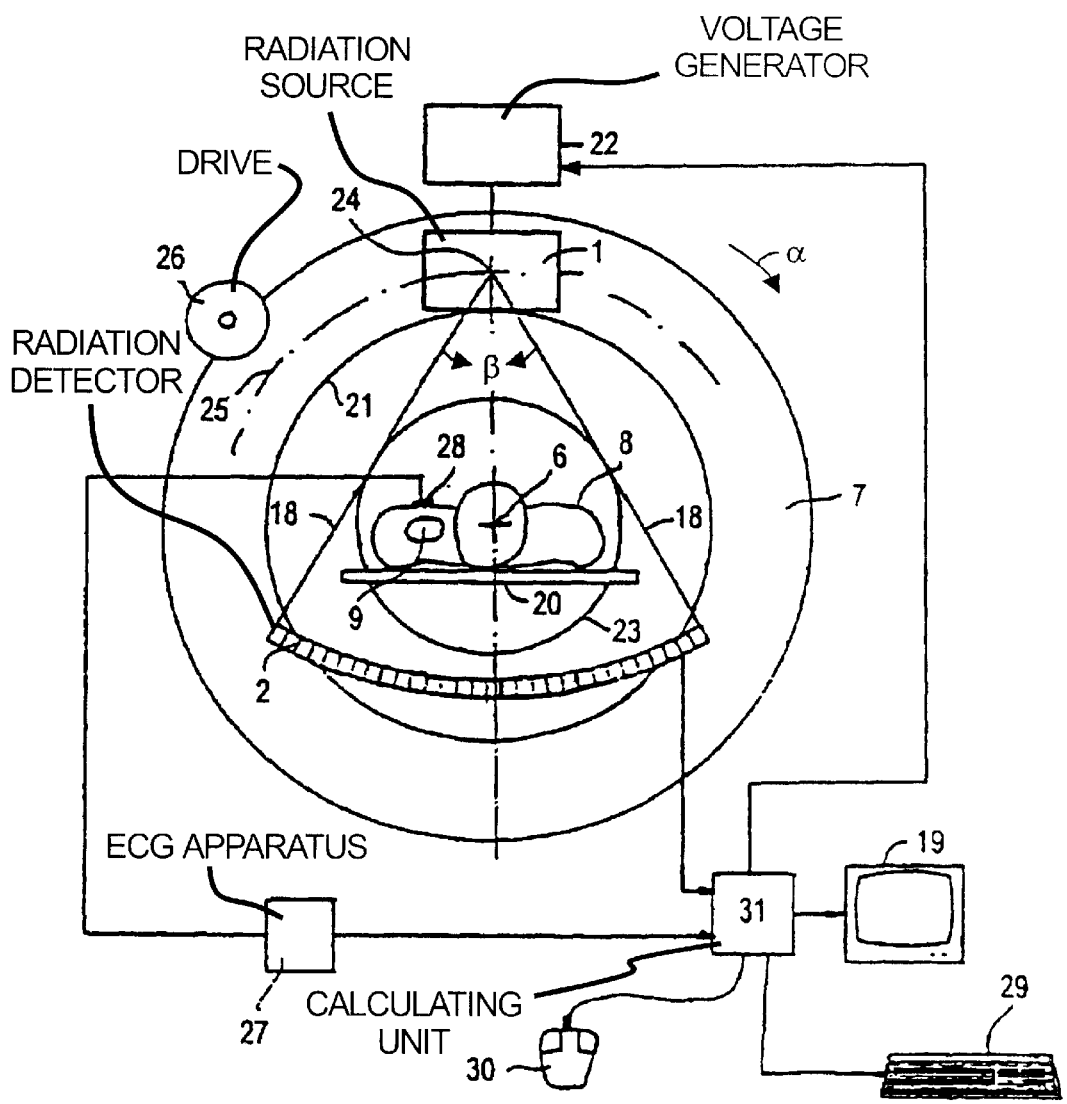
FIG. 1, is a block diagram of a CT apparatus for the implementation of the inventive method
Figure 2:
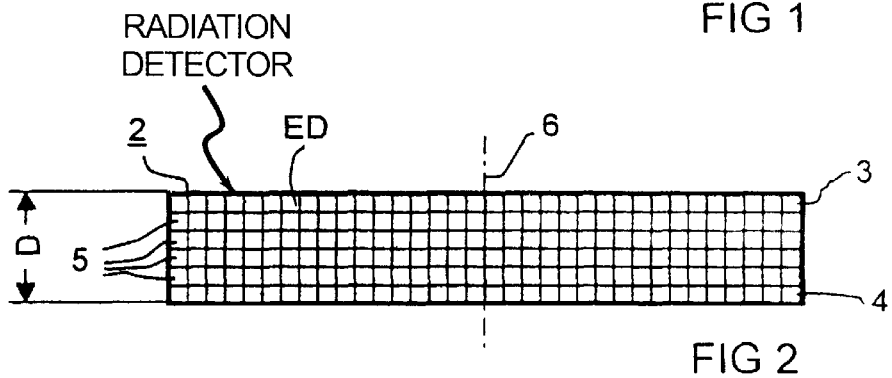
FIG. 2 is a view of the detector unit of the CT apparatus according to FIG. 1.

FIGS. 1 and 2 schematically show a CT apparatus for the implementation of the inventive method.

The CT apparatus has a measuring unit composed of an x-ray source 1 that emits an x-ray beam 18 and a detector unit 2 that is composed of a number of lines of individual detectors following one another in the direction of a rotational axis 6, for example each line having 512 individual detectors. The focus of the x-ray source 1, from which the x-ray beam 18 emanates, is referenced 24. The examination subject, a human patient 8 in the case of the illustrated exemplary embodiment, lies on a positioning table 20 that extends through the measuring opening 21 of an annular carrier 7, referred to as the gantry.

As shown in FIG. 2, the detector unit 2 has a first detector line 3 and a last detector line 4. One or—as shown—more further detector lines 5 as well can be arranged between the first and the last detector lines 3, 4.

The detector lines 3 through 5 proceed at a right angle relative to the rotational axis 6, which is indicated dot-dashed in FIG. 2. The first detector line 3 and the last detector line 4 are spaced from one another by a detector width D parallel to the rotational axis 6. The detector width D is measured from cell middle to cell middle.

The x-ray source 1 and the detector unit 2 are attached to the carrier 7 opposite one another such that the x-ray beam 18 emanating from the x-ray source 1 strikes the detector unit 2. The carrier 7 is rotatable around the rotational axis 6 of the CT apparatus, which represents the system axis, and rotates with a speed n around this rotational axis 6 for scanning the patient 8. The x-ray beam 18 emanating from the x-ray source 1 operated with a voltage generator 2 thereby covers a measuring field 23 having a circular cross-section. The focus 24 of the x-ray source 1 moves on a focus path 25 that is circularly curved around a rotational center lying on the rotational axis 6.

The x-ray beam 18 transirradiates the patient 8 and the x-rays arriving at the detector unit 2 are detected during the rotation at a number of projection angles α, and the output data of the individual detectors for each of the detector lines 3 through 5 are combined to form a projection belonging to the respective projection angle α. A number of projections corresponding in number to the number of detector lines 3 through 5 thus belongs to every projection angle α.

Using the projections that proceed from the detector unit 2 to an electronic calculating unit 31 and that are registered during a reconstruction interval which can cover a number of data intervals, the electronic calculating unit 31 reconstructs a tomogram of a subject under examination with known algorithms. In order to be able to meaningfully reconstruct tomograms of the subject under examination, the registration of projections at successive projection angles α is required that extend over a reconstruction interval that must be at least equal to 180°+β, whereby β is the aperture angle of the x-ray beam 18 shown in FIG. 1, which is also referred to as the fan angle.

As mentioned, the drive 26 allocated to the carrier 7 is suitable for allowing the carrier 7 to rotate continuously. Moreover, another drive (not shown in the Fig.) is provided that enables a relative displacement of the positioning table 20 and, thus, of the patient 8, and the carrier 7 with the measuring unit 1, 2, in the direction of the rotational axis 6 with a feed velocity v.

There is thus the possibility of scanning three-dimensional regions of the patient 8 in the form of a spiral scan, with the carrier 7 together with the measuring unit 1, 2 rotates continuously and a relative displacement of positioning table 20 and carrier 7 simultaneously ensues in the direction of the rotational axis 6 with the feed velocity v.

For implementing examinations of the heart or of heart-proximate regions of the body of the patient 8 moving in the rhythm of the heart action, the CT apparatus according to FIG. 1 also has a known electrocardiograph apparatus 27 that can be connected to the patient 8 via electrodes (one is shown in FIG. 8 and referenced 28) and that serves for the acquisition of the ECG signal of the patient 8 in parallel with the examination with the CT apparatus. Data preferably digital data, corresponding to the ECG signal are supplied to the electronic calculating means 31.

The electrodes of the electrocardiograph apparatus 27 are attached to the body of the patient 8 such that, insofar as possible, they do not negatively influence the examination of the patient 8.

Insofar as body parts of the patient 8 that can be placed at rest are to be registered, no noteworthy problems arise for the registration of the projections. The registration of projections of a periodically moving subject, however, is critical. An example of such a subject is the human heart 9, which is schematically shown in FIG. 1.

As known, the human heart 9 executes essentially a periodic motion. The periodic motion is composed of an alternating sequence of a quiescent or relaxation phase and a motion or beating phase. The relaxation phase usually has a duration between 500 through 800 ms; the beating phase has a duration of 200 through 250 ms.

The rotational speed n of the carrier 7 usually is between 45 through 120 revolutions per minute. By comparing the speed n to the duration of the relaxation phase of the heart 9, it can thus easily be found that the carrier 7 rotates through a rotational angle γ in the relaxation phase of the heart 9 that is between 135° (500 ms given 45 rpm) and 576° (800 ms given 120 rpm).

When the speed n is selected high enough, the carrier 7 rotates through an angle during the respective phase of a cardiac cycle to be registered, for example during a quiescent phase, that is larger than the required reconstruction interval. It is thus possible to register the projections required for the reconstruction of a tomogram of the registered region of the heart 9 during the phase of a cardiac cycle to be registered.

When the heart frequency is so high that it is not possible to register the projections belonging to a complete reconstruction interval during a single cardiac cycle, this can ensue during the phase to be registered in a number of successive cardiac cycles. The reconstruction interval is then composed of a number of data intervals belonging to different cardiac cycles.

As already mentioned, the electrocardiogram 10 of the human heart 9 is simultaneously registered in order to be able to determine the quiescent phases 13 of the human heart therefrom.

In the inventive method, the ECG signal is used to modulate the intensity of the x-rays emanating from the x-ray source 1, for example an x-ray tube, according to a trapezoidal curve such that it reaches its rated value $I_0$ only during the phase of the cardiac cycle to be registered, for example during the quiescent phases of the heart 9, and is otherwise substantially lowered, for example to $I_0/5$. This is achieved by the electronic calculating unit 31 connected to the voltage generator 22, for example by a corresponding modulation of the tube current of the x-ray source 1.

In this way, the radiation load on a patient 8 is reduced, since the application of x-rays with full intensity is limited to those time intervals, namely the reconstruction or data intervals, wherein projections useable for image reconstruction are registered.

Figure 3:
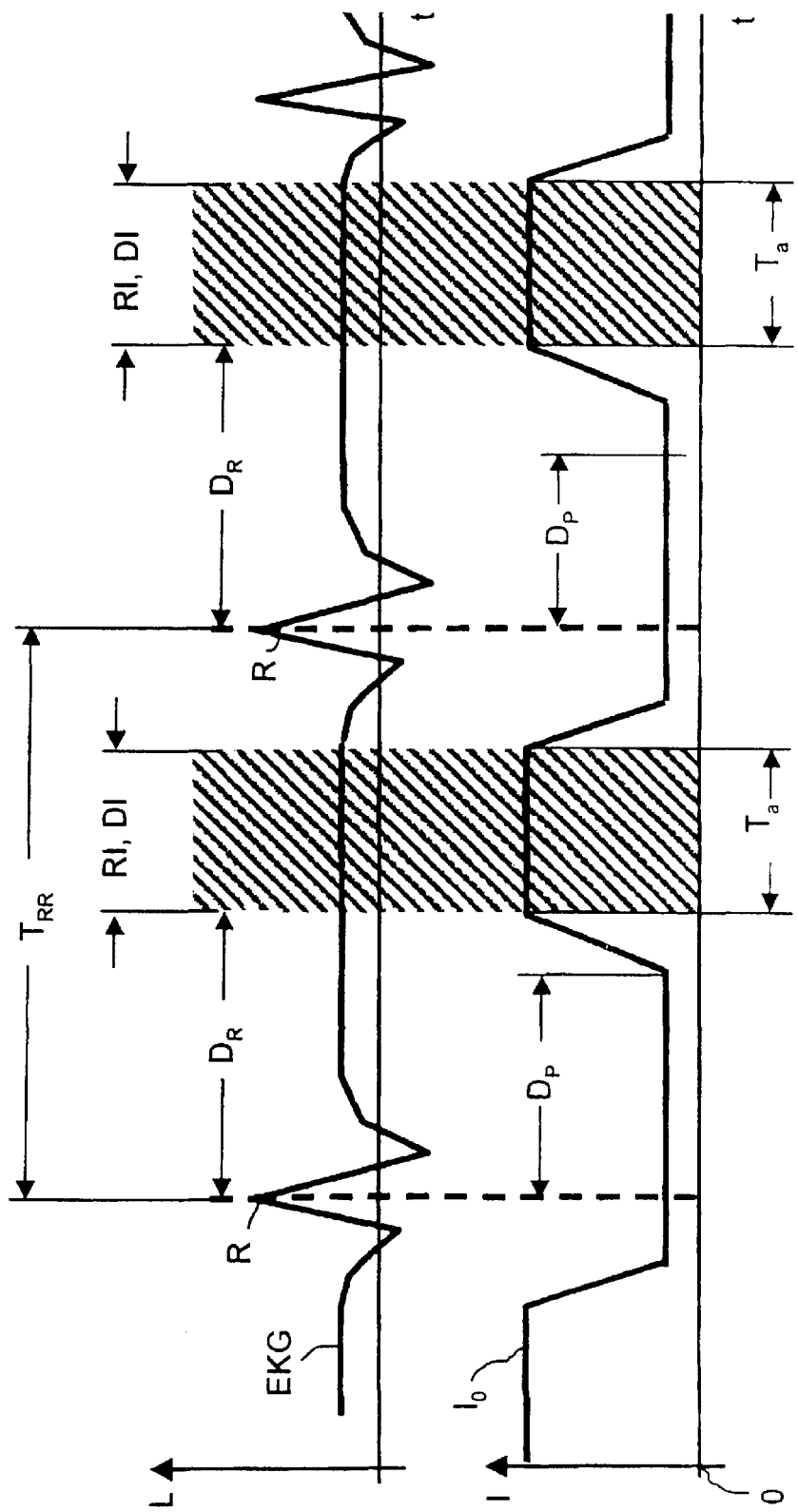
FIGS. 3 and 4 are diagrams illustrating the functioning of the inventive method.

This can be seen from FIG. 3 wherein the level L of the ECG signal of a patient and the intensity I of the x-rays emanating from the x-ray source 1 are shown above one another over the time t. The ECG signal illustrates the periodic movement of the heart of the patient, with the beginning of a cardiac cycle is being defined by an R-wave R and the duration of the respective cardiac cycle is defined by the R-R interval, i.e. the distance of the R-wave initiating the cardiac cycle from the R-wave initiating the following cardiac cycle. The quiescent phase of the heart to be registered in the illustrated example is indicated hatched.

As is apparent from the curve of the intensity I of the x-radiation that changes between the reference value $I_0$ and the lowered value $I_0/5$, the x-ray source 1 is modulated such that the reference value 10 is effective only during the cardiac phase to be registered, i.e. the quiescent phase.

This occurs by elevating the intensity I of the x-rays prospectively, by a delay time $D_I$ after the occurrence, to the reference value $I_0$ for a time duration $T_a$.

The time duration $T_a$, during which projections are registered for a full-revolution or partial-revolution scan, can be a complete reconstruction interval RI or only a data interval DI.

The delay time $D_I$ and the time duration $T_a$ are determined by the electronic calculating unit 31 which determines the average of the duration of the R-R intervals $T_{RR}$ from a pre-selectable number of preceding R-R intervals and determines the delay time $D_I$ and the time duration $T_a$ therefrom as pre-selectable percentages or fractions of this average. Alternatively, the delay time $D_I$ and the time duration $T_a$ can be preselected as time durations, for example in milliseconds.

Taking the average of the duration of the R-R intervals $T_{RR}$ from a pre-selectable number of preceding R-R intervals into consideration, the electronic calculating unit 31 sets the feed velocity v such that the shift of the positioning table 20 in the direction of the system axis 6, i.e. the displacement of the measuring unit 1, 2 and of the patient 8 relative to one another in the direction of the system axis 6, that occurs during a reconstruction interval RI or data interval DI does not exceed a detector width D (see FIG. 2). The regions of the patient 8 covered by successive reconstruction intervals RI or data intervals DI thus overlap in the direction of the system axis 6 or, in the limiting case, adjoin one another gap-free. The entire volume of the patient 8 scanned in the direction of the system axis thus can be covered gap-free with tomograms.

For a reconstruction of a 3D image in a specific phase of the cardiac cycle (for example, the diastole, i.e. quiescent phase), only projections of this phase are utilized for the reconstruction, as illustrated in FIG. 3. The selection of the projections ensues with a specific time spacing DR from the most recent R-wave, which can be determined, for example, retrospectively at a fixed fraction of the known R-R interval length $T_{RR}$.

As an example, FIG. 3 shows a trapezoidal modulation curve for the intensity I of the x-rays. Other modulation curves (for example, rectangular or sinusoidal) are also possible. The ECG-based modulation of the intensity I of the x-rays to the reference value $I_0$ must ensue prospectively while estimating the current R-R interval length $T_{RR}$ with a specific time spacing from the most recent R-blip. The corresponding delay $D_I$ is to be correspondingly adapted in conformity with the desired heart phase. The R-R interval length $T_{RR}$ currently valid after a R-wave can, for example, be approximately determined from the preceding cardiac cycle. A dose reduction of approximately 50% is achieved in the example of FIG. 3 for an R-R interval length $T_{RR}$ of one second and a time duration $T_a$=350 msec during which the intensity I of the x-rays exhibits its reference value $I_0$ in every cardiac cycle.

Figure 4:
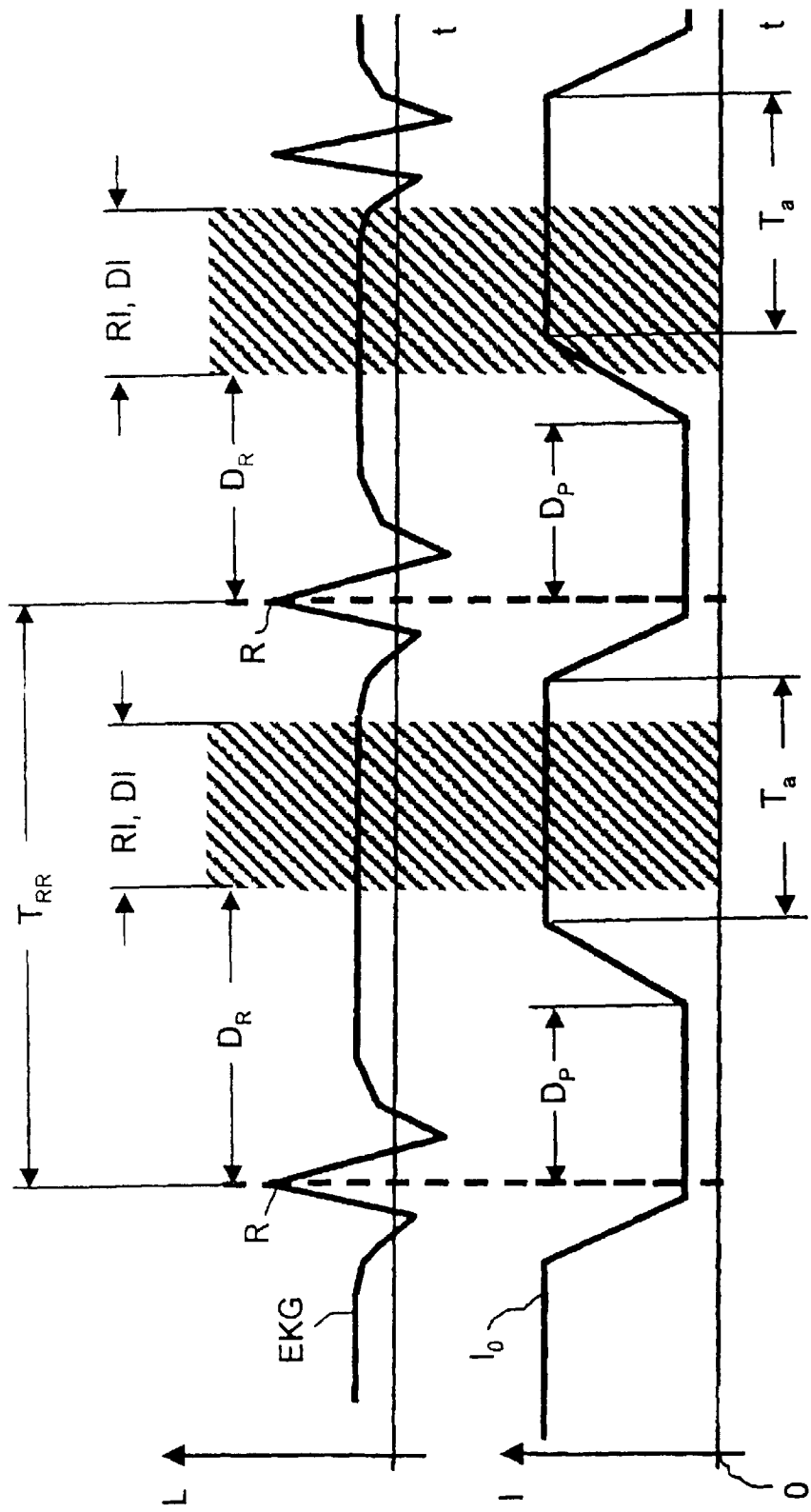

Of necessity, the modulation of the intensity I of the x-rays ensues in real time during the registration of the projections. The time delay $D_1$ after which the intensity I of the x-rays is stepped up to the reference value $I_0$ is usually defined from the prospectively estimated R-R interval length $T_{RR}$ of the respective cardiac cycle (for example: $D_I$=0.5 $T_{RR}$ for the diastole). As shown in FIG. 4, prospectively estimated and actual R-R interval lengths $T_{RR}$ can deviate substantially given patients with heart rate arrhythmia. Nonetheless, losses in image quality that are thus produced can be avoided with an ECG-controlled dose modulation.

As shown in FIG. 4, the time interval $T_a$ wherein the intensity I of the x-rays exhibits the reference value $I_0$ can be longer than the time duration of the required reconstruction interval RI or data interval DI. Phase inconsistencies then can be prevented by retrospective adaptation of the time position of the reconstruction interval RI or of the data interval DI using the delay DR determined from the actual R-R interval lengths $T_{RR}$. The retrospectively placed reconstruction interval RI or data interval DI also can employ projections that were registered with an intensity of the x-rays below the reference value $I_0$, as shown in FIG. 4.

The non-uniform noise impression which then occurs in the images is balanced against the artifacts that are caused by reconstruction in inconsistent phase of the heart cycle. Given slight losses in the image sharpness, non-uniform image noise can be avoided by an adaptive filtration of the projections p(k) given I<$I_0$, for example according to equations (1a) through (1c).

$$p_{af}(k) = Ap_f(k) + (1-A)p(k) \tag{1a}$$

$$\text{with} \quad p_f(k) = p(k) * tp(k) \tag{1b}$$

$$\text{and} \quad A = 1 - F(I/I_0) \tag{1c}$$

As disclosed in U.S. Pat. No. 4,707,786, the adaptively filtered projection $p_{af}(k)$ is calculated, for example, by "mixing" the original projection p(k) with a filtered projection $p_f(k)$. The projection $p_f(k)$ thereby results from the filtering of p(k) with the pulse response of a low-pass filter tp(k) in the spatial domain. The "mixing ratio" A depends—via the function F(.)—on the ratio of the tube current 1 to the reference value $I_0$. For example F(1/10)=1 and A=0 are valid for I=$I_0$. However, other types of adaptive filtration are also possible.

The technique of selecting the duration during which the intensity of the x-radiation exhibits its reference value $I_0$ longer following a trigger pulse than the time duration of the required reconstruction interval RI or data interval DI, also can be applied to spiral scans with prospectively triggered acquisition of the projections. Analogous to FIG. 2, the time position of the reconstruction interval RI or data interval DI in the cardiac cycle also can be adapted here. However, no projections beyond the acquisition window can be employed.

Other physiological parameters or signals that provide information about the current phase of the cardiac cycle, for example movement of the cardiac wall or stethoscopic heartbeat analysis, can be employed instead of the ECG signal.

The invention has been explained above with regard to the example of heart examinations, however, other periodically moving body regions also can be examined with the inventive method.

A CT apparatus of the third generation is employed in conjunction with the above specification of the invention, i.e. the x-ray source and the detector unit are displaced in common around the system axis during the image generation. The invention, however, also can be employed in conjunction with a CT apparatus of the fourth generation wherein only the x-ray source is displaced around the system axis and interacts with a stationary detector ring, insofar as the detector ring has a number of detector lines.

Other than being employed in computed tomography, the invention also can be utilized in imaging methods that operate with penetrating radiation.

The invention was explained above with regard to a medical application. The invention, however, can also be employed in fields other than medicine.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for examining a body region that executes a periodic motion in an examination subject, comprising the steps of:
   irradiating said body region with radiation which penetrates said body region;
   detecting said radiation after penetrating said body region with a detector system and emitting output data from said detector system corresponding to radiation incident on said detector system;
   modulating an intensity of said radiation between a reference value and a non-zero reduced value, that is reduced compared to said reference value, substantially synchronously with said periodic motion so that said reference value is present during a phase of said periodic motion; and
   electronically calculating an image of said body region using only output data from
   said detector system obtained while said radiation has said intensity at said reference value.

2. A method as claimed in claim 1 comprising obtaining a signal from said examination subject representing said periodic motion, and modulating said intensity of said radiation dependent on said signal.

3. A method as claimed in claim 2 comprising modulating said intensity of said radiation from said reduced value to said reference value with a first delay after a beginning of a period of said signal, and modulating the intensity of the radiation from said reference value to said reduced value at a second delay time after said beginning of said period of said signal, said first delay time being shorter than said second delay time.

4. A method as claimed in claim 2 comprising determining an average duration of a period of said signal, and modulating the intensity of the radiation from said reduced value to said reference value at a first fraction of said period after a beginning of said period, and modulating the intensity of the radiation from said reference value to said reduced value at second fraction of said period of said signal after said beginning of said period of said signal, said first fraction being smaller than said second fraction.

5. A method as claimed in claim 1 wherein, in each period of said periodic motion, a data interval is required to acquire said output data for producing said image, and comprising modulating said radiation to have said reference value for a time duration which is longer than a duration of said interval.

6. A method as claimed in claim 1 wherein, in each period of said periodic motion, an interval is required to acquire said output data for producing said image, and comprising acquiring said output data for an acquisition interval which is longer than said interval.

7. A method as claimed in claim 1 comprising acquiring a signal from said examination subject representing said periodic motion, storing said signal and storing said output data correlated in time with each other, and identifying said output data which were obtained during said phase when said intensity value was at said reference value by identifying said phase in said signal.

8. A method as claimed in claim 1 comprising adaptively filtering said output data for noise reduction that are employed for producing said image.

9. A method as claimed in claim 1 comprising mounting said radiation source and said radiation detector for rotation around a system axis of a computed tomography apparatus, and rotating said radiation source and said detector system around said system axis while irradiating said examination subject with said radiation.

10. A method as claimed in claim 9 comprising relatively displacing said x-ray source and said detector system, and said examination subject, while irradiating said examination subject with said radiation during rotation of said radiation source.

11. A method as claimed in claim 10 comprising forming said detector system of a plurality of detector lines, including a first detector line and a last detector line, and spacing said first detector line from said last detector line along said system axis by a detector width.

12. A method as claimed in claim 11 comprising relatively displacing said x-ray source and said detector system, and said examination subject, with a feed velocity along said system axis so that relative displacement in an interval during which said output data are acquired does not exceed said detector width.

13. A method as claimed in claim 1 comprising irradiating a body region of said examination subject containing a lung.

14. A method as claimed in claim 1 comprising irradiating a body region of said examination subject containing a heart.

15. A method as claimed in claim 14 comprising obtaining an ECG signal from said examination subject and modulating said intensity dependent on said ECG signal.

* * * * *